(12) United States Patent
Tu et al.

(10) Patent No.: US 7,375,052 B2
(45) Date of Patent: May 20, 2008

(54) PROCESS FOR PRODUCING METAL OXIDE CATALYST

(75) Inventors: Xinlin Tu, Nagoya (JP); Yuuichi Sumida, Nagoya (JP); Mamoru Takahashi, Nagoya (JP); Hiroshi Niizuma, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 417 days.

(21) Appl. No.: 10/553,397

(22) PCT Filed: Apr. 13, 2004

(86) PCT No.: PCT/JP2004/005264

§ 371 (c)(1),
(2), (4) Date: Oct. 17, 2005

(87) PCT Pub. No.: WO2004/091779

PCT Pub. Date: Oct. 28, 2004

(65) Prior Publication Data

US 2007/0161767 A1 Jul. 12, 2007

(30) Foreign Application Priority Data

Apr. 16, 2003 (JP) ............................. 2003-112137

(51) Int. Cl.
*B01J 23/00* (2006.01)
*C07C 51/16* (2006.01)
*C07C 253/00* (2006.01)

(52) U.S. Cl. ...................... 502/305; 502/312; 562/549; 558/332

(58) Field of Classification Search ...................... None
See application file for complete search history.

(56) References Cited

U.S. PATENT DOCUMENTS

2006/0047137 A1* 3/2006 Tu et al. ...................... 558/338

FOREIGN PATENT DOCUMENTS

JP 59227703 * 12/1984
JP 11-226408 A 8/1999

* cited by examiner

*Primary Examiner*—Karl Puttlitz
(74) *Attorney, Agent, or Firm*—Sughrue Mion, PLLC

(57) ABSTRACT

The present invention relates to a process for producing a metal oxide catalyst which is suitable for production of acrylic acid or acrylonitrile in one stage by a catalytic oxidation reaction of propane in a high yield.

The present invention is characterized by using a fine particle of metallic tellurium obtained by reducing a Te compound with a reductant as a raw material for producing an oxide catalyst including metal elements Mo—V—Nb—Te. The fine particle of metallic tellurium is preferably one containing primary particles having a particle size of not more than 4.0 μm. By using a metal oxide obtained by the process of the present invention, acrylic acid can be produced from propane by a one-stage oxidation reaction in a higher yield not less than 40%.

6 Claims, 3 Drawing Sheets

PROCESS FOR PRODUCING METAL OXIDE CATALYST

TECHNICAL FIELD

It is known that acrylic acid is produced in one stage by vapor phase oxidation of propane. This production process has an advantage of using cheap propane as a raw material comparing with a process for producing acrylic acid using propylene which has hitherto been known. In the oxidation reaction for producing acrylic acid from propane, it was general that a metal oxide catalyst is used. In the present invention, a process is proposed for producing a metal oxide to be used in the oxidation reaction for producing acrylic acid from propane. By using the metal oxide obtained by the production process of the present invention as a catalyst for foregoing oxidation reaction, acrylic acid can be produced in a high yield.

BACKGROUND ART

In general, acrylic acid is produced by a two-stage oxidation reaction of undergoing catalytic reaction of propylene with oxygen in the presence of a catalyst to produce acrolein and undergoing catalytic reaction of the resulting acrolein with oxygen.

In the recent years, due to a price difference between propane and propylene and for the purpose of overcoming problems such as complexity in the process involving the two-stage oxidation, a process for producing acrylic acid in one stage by using propane as a starting raw material is studied, and there have been made a number of proposals with respect to catalysts to be used therefor. As representative examples thereof, there are enumerated catalysts made of a composite metal oxide such as [V, P, Te] bases, [Mo, Te, V, Nb] bases, and [Mo, Sb, V, Nb] bases.

Recently, there have been filed some applications for patent with respect to further improvements of the foregoing metal oxide catalysts. JP-A-10-137585 discloses a process for producing a catalyst by mixing an aqueous solution obtained by allowing a molybdenum compound, a vanadium compound and an antimony compound to react in an aqueous medium at 70° C. or higher with a niobium compound, evaporating to dryness the resulting mixture, and further calcining it at a high temperature.

JP-A-10-230164 describes that in heating the respective metal compounds in the aqueous medium described in the foregoing JP-A-10-137585, a gas containing molecular oxygen is introduced into the aqueous medium. Furthermore, it is described that when the catalyst as produced in this process is used for vapor phase catalytic oxidation reaction of propane, the yield of acrylic acid is enhanced.

Also, JP-A-11-285636 describes that hydrogen peroxide is added to a reaction liquid of the respective metal compounds in the aqueous medium during heating and reaction, or after the reaction as described in the foregoing JP-A-10-137585 and JP-A-10-230164.

However, even in the case of using the catalysts as described in all of the foregoing patent documents, the yield of acrylic acid as obtained in one-stage oxidation of propane does not reach a practical level required in the acrylic acid production.

JP-A-11-226408 discloses a method for allowing a metallic tellurium power to react with an oxonic acid salt (oxometalate) of other element, such as ammonium metavanadate, molybdic acid, and ammonium paramolybdate, in an aqueous medium, thereby dissolving the subject metal powder in a reaction liquid and using the resulting reaction liquid as a raw material of a metal oxide catalyst. However, the particle size of the tellurium particle to be used in the invention as described in the subject patent document exceeded 100 µm, and a long period of time was required for the reaction in the aqueous medium. Furthermore, when the resulting metal oxidation catalyst is used in ammoxidation of propane, it is possible to produce acrylonitrile in a propane conversion of from 25 to 30% and a selectivity of approximately 60%. However, when used for the reaction for producing acrylic acid from propane, there was no drastic advance in performance as compared with conventionally known catalysts.

DISCLOSURE OF THE INVENTION

In order to obtain a catalyst capable of producing acrylic acid and acrylonitrile in one stage by a catalytic oxidation reaction of propane in a high yield, the present inventors made extensive and intensive investigations. As a result, they have found a metal oxide catalyst obtainable from the following production processes.

Specifically, the invention relates to a process for producing a metal oxide catalyst represented by the following composition formula, which is characterized by allowing a fine particle of metallic tellurium as obtained by reducing a $Te^{4+}$ compound or a $Te^{6+}$ compound in the presence of a reductant and water or an organic solvent to react in the presence of an Mo compound, a V compound, a compound containing an A element and water and then drying and calcining.

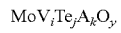   Composition formula: $MoV_iTe_jA_kO_y$ (In the formula, A is at least one element selected from Nb, Ta, W, Ti, Zr, Re, Fe, Ni, Co, Sn, Tl, Cu, rare earth elements, and alkali metal elements. i and j are each from 0.01 to 1.5, and j/i is from 0.3 to 1.0; k is from 0.001 to 3.0; and y is the number to be determined by the oxidized state of other elements.)

Also, the invention is concerned with a process for producing a metal oxide catalyst represented by the following composition formula, which is characterized by employing a process comprising the following step (1), step (2), step (3), step (4) and step (5).

Step (1): A step for reducing a $Te^{4+}$ compound or a $Te^{6+}$ compound in the presence of a reductant and water or an organic solvent to obtain a dispersion containing a fine particle of metallic tellurium.

Step (2): A step for removing the unreacted reductant and organic solvent contained in the foregoing dispersion as obtained in the foregoing step (1) to obtain an aqueous dispersion containing a fine particle of metallic tellurium.

Step (3): A step for mixing the aqueous dispersion containing a fine particle of metallic tellurium as obtained in the foregoing step (2) with an $Mo^{6+}$ compound and a $V^{5+}$ compound and allowing the mixture to react at a temperature of 40° C. or higher for one hour or more to obtain a reaction liquid.

Step (4): A step for mixing the reaction liquid as obtained in the foregoing step (3) with a compound containing the following A element to obtain a mixed liquid.

Step (5): A step for evaporating to dryness the mixed liquid as obtained in the foregoing step (4), drying the resulting dried material and further calcining it.

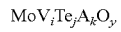   Composition formula: $MoV_iTe_jA_kO_y$ (In the formula, A is at least one element selected from Nb, Ta, W, Ti, Zr, Re, Fe, Ni, Co, Sn, Tl, Cu, rare earth elements, and alkali metal elements. i and j are each from 0.01 to 1.5, and j/i is from 0.3 to 1.0; k is from 0.001 to 3.0; and y is the number to be determined by the oxidized state of other elements.)

The foregoing production processes include an invention wherein a primary particle of the metallic tellurium has a size of not more than 4.0 μm.

In addition, the invention is concerned with a process for producing acrylic acid or acrylonitrile, which is characterized by subjecting propane to oxidation or ammoxidation by vapor phase catalytic reaction in the presence of the metal oxide catalyst as produced by the foregoing processes.

BEST MODE FOR CARRYING OUT THE INVENTION

Figure 1:
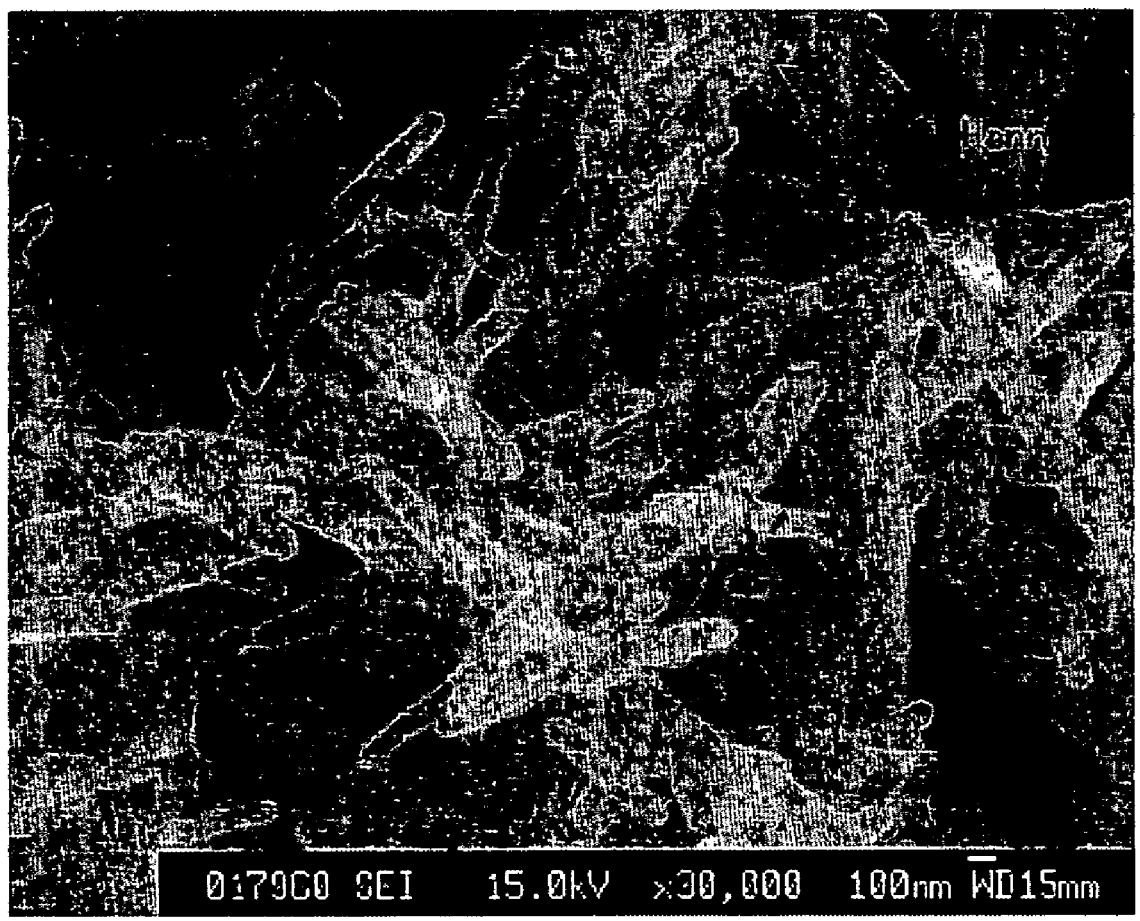
FIG. 1 shows an SEM (scanning electron microscope) image of metallic tellurium particles as obtained in Example 1.

In the invention, as a raw material for the production of a catalyst which is used in the vapor phase catalytic oxidation reaction of propane, a fine powder of metallic tellurium as obtained by reducing a $Te^{4+}$ compound or a $Te^{6+}$ compound (a tellurium compound having a valence of 4 or 6) in the presence of a reductant and water or an organic solvent.

Preferred embodiments of the invention will be hereunder described while dividing into steps (1) to (5). Incidentally, in the respective steps, technical means which are known in this field, such as heat treatment, coprecipitation, drying, calcination, and hydrothermal synthesis, can be employed without limitations.

Step (1)

In this step, a $Te^{4+}$ compound or a $Te^{6+}$ compound is reduced in the presence of a reductant and water or an organic solvent to obtain a dispersion containing a fine particle of metallic tellurium.

The $Te^{4+}$ compound or $Te^{6+}$ compound (a tellurium compound having a valence of 4 or 6) is not particularly limited, and specific examples thereof include tellurium dioxide, tellurium trioxide, tellurium tetrachloride, orthotelluric acid, metatelluric acid, polymetatelluric acid, ammonium tellurate, alkali metal tellurate, zinc tellurate, calcium tellurate, silver tellurate, thallium tellurate, copper tellurate, and magnesium tellurate.

Incidentally, in the invention, since noxious elements such as chlorine can be removed in the subsequent step (2), chlorine compounds can be used as the $Te^{4+}$ compound or $Te^{6+}$ compound.

As reductants, any reducing substances (atoms, molecules or ions to be capable of providing other molecule with electrons) having an oxidation-reduction potential against a standard electrode of not higher than 0.53 V (the potential of tellurium dioxide is in the vicinity of 0.53 V) can be used.

Hydrazine, hydradinium salts, hydroxylamines, and the like are preferable in view of reactivity of the reduction reaction or because they do not act to water. Specific examples thereof include hydrazine acetate, hydrazine dihydrobromide, hydrazine dihydrochloride, hydrazine monohydrochloride, hydrazine monohydrate, hydrazine sulfate, hydroxylamine, hydroxylammonium chloride, and hydroxyl-ammonium sulfate.

For example, when hydrazine is used, the molar ratio of hydrazine to tellurium is preferably from 0.5 to 4.0, and more preferably from 1.0 to 3.0. When the amount of hydrazine added is less than 0.5 mole, unreacted tellurium dioxide remains in a large amount. On the other hand, when the amount of hydrazine added exceeds 4.0 moles, or more, there is no advantage at all. Rather, in order to remove unreacted hydrazine, excessive labors and rinsing liquids are required. In the case of other reductants than hydrazine, the amount of their addition substantially follows that of hydrazine.

The reduction reaction is carried out in a liquid such as water and an organic solvent. As the organic solvents, alcohols, hydrocarbons, and the like are preferable. With the presence of the solvents, the tellurium compound is dispersed so that the reduction reaction becomes easy to proceed. As a result, the resulting particle of metallic tellurium becomes uniform.

The reduction condition of the tellurium compound is adequately chosen by examining the solubility of the tellurium compound to be used in water or an organic solvent, etc. and the reactivity of the reductant. For example, in the case where water-soluble telluric acid is used as the starting tellurium compound and hydrazine as the reductant, respectively, only by adding hydrazine into an aqueous solution of telluric acid at room temperature, the reduction reaction occurs, whereby a fine particle of metallic tellurium is formed in water.

In the case where tellurium dioxide, a tellurium compound having poor solubility in organic solvents, is used as the staring tellurium compound and hydrazine as the reductant, the rate of the reduction reaction is low. In this case, it is necessary to promote the reaction by stirring and heating over a long period of time. Specifically, the reaction is carried out at a temperature of from 40° C. to the boiling point of water and at stirring rate of from 100 to 500 rpm for from 1 to 20 hours, and preferably at a temperature of from 60° C. to the boiling point of water and at a stirring rate of from 200 to 300 rpm for from 2 to 10 hours.

Furthermore, as a method for promoting the reduction reaction, besides heating or stirring, there is a wet-type grinding method in the copresence of a tellurium compound, a reductant, and water and/or an organic solvent. In this way, the reduction reaction and the grinding proceed at the same time, and more finely particulate metallic tellurium is obtained. As a result, good influences are given to the performance of the resulting catalyst.

Though the organic solvent which is used during the grinding is not particularly limited, organic solvents which are liquid at the ambient temperature and can be easily removed in post steps are preferable. Specifically, alcohols such as methanol, ethanol, and propanol, and hydrocarbons such as hexane, cyclohexane, and toluene are preferable. When water or the organic solvents are present at the time of grinding, the increase of the surface energy accompanying the grinding is relieved, and grinding efficiency is enhanced.

With respect to a mixing proportion of water or the organic solvent to the tellurium compound at the time of grinding, water or the organic solvent is preferably used in an amount of from 10 to 1,000 parts by mass, and more preferably from 30 to 300 parts by mass based on 100 parts by mass of the tellurium compound. When the mixing proportion of water or the organic solvent to the metal A is less than 10 parts by mass, ground material adheres to the grinding vessel so that the grinding becomes difficult. Also, when it exceeds 1,000 parts by mass, the solvent absorbs the impact during the grinding so that grinding efficiency is lowered.

For a grinding machine, a mode by which grinding is conducted by driving the vessel per se containing the material to be ground is preferable. Specifically, there are enumerated a ball mill, a vibration mill, and a planetary ball mill. Grinding time is suitably from 0.5 to 24 hours.

When a powder which is obtained by drying a solid as obtained by the foregoing reduction reaction is subjected to powder X-ray diffraction analysis, it is understood that the subject solid is a crystal of pure hexagonal metallic tellurium.

When the foregoing dried powder of metallic tellurium is observed by an electron microscope, with respect to the appearance of the primary particle, a spherical particle or an acicular particle is observed depending upon the difference of the reduction method. Any primary particle has a very narrow particle size distribution. Furthermore, though agglomeration of the primary particle is seen depending upon the sample to be observed, this can be generated at the time of drying and does not affect the production of a catalyst and the performance of the resulting catalyst.

The size of the primary particle of metallic tellurium as obtained by the foregoing reduction reaction is in the range of not more than 4.0 μm, and preferably not more than 2.0 μm in at least one direction. Though a lower limit of the size of the primary particle is not particularly present, it is preferably 0.01 μm or more from the viewpoint of easiness of the operation. When the size of the primary particle is more than 4.0 μm, dispersibility of the metallic tellurium particle in water or the organic solvent becomes worse so that the production of a catalyst is likely adversely affected thereby.

Step (2)

In the step (2), the unreacted reductant contained in the dispersion containing the metallic tellurium fine particle as obtained in the step (1) is removed. When the organic solvent is used as a medium of the reduction reaction, the solvent is removed, and water is then added to obtain an aqueous dispersion. As a method for removing the unreacted reductant and organic solvent, there are enumerated a method for evaporating off the reductant and organic solvent in vacuo and a method for separating and removing the reductant and organic solvent by centrifugation or filtration operation. After the removal, by re-dispersing the resulting metallic tellurium fine particle in water, it is possible to obtain an aqueous dispersion of the metallic tellurium fine particle.

It is important that the reductant does not remain in the resulting aqueous dispersion, and it is preferable that the metallic tellurium fine particle as obtained by filtration is thoroughly washed with water and then dispersed in water to obtain an aqueous dispersion.

With respect to a concentration of the solid in the aqueous dispersion, the amount of water is preferably from 10 to 100 liters per mole of the metallic tellurium fine particle.

Step (3)

In the step (3), the aqueous dispersion containing the metallic tellurium fine particle as obtained in the foregoing step (2) is mixed with an $Mo^{6+}$ compound and a $V^{5+}$ compound, and the mixture is allowed to react at a temperature of 40° C. or higher for one hour or more.

Examples of the $Mo^{6+}$ compound include ammonium molybdate, molybdenum oxide, and molybdic acid. Of these compounds, ammonium molybdate is preferable because it is soluble in water.

As the $V^{5+}$ compound, ammonium metavanadate, vanadium pentoxide, and the like are preferable.

With respect to addition amounts of the $Mo^{6+}$ compound and the $V^{5+}$ compound, an atomic ratio (i and j) of V and Te to Mo is from 0.01 to 1.5, respectively, and an atomic ratio (j/i) of Te to V is from 0.3 to 1.0. When Mo, V and Te fall outside the foregoing ranges, it is impossible to obtain a metal oxide catalyst with an expected performance.

For the purposes of improving the operability, etc., the aqueous dispersion may be diluted by further adding water thereto. A reaction temperature is 40° C. or higher, and preferably from 40 to 100° C. A heating time is preferably from 1 to 10 hours, and more preferably from 2 to 5 hours. It is preferable that the aqueous dispersion is stirred during the reaction.

Step (4)

In the step (4), a reaction liquid as obtained in the foregoing step (3) is mixed with a compound containing a metal element A as described later (hereinafter referred to as "A-containing compound"). Though mixing temperature is not particularly limited, it may be usually room temperature. It is preferable that the metal element A is mixed in the state of an aqueous solution or an aqueous dispersion. In this case, since a fine precipitate is formed during this mixing, the mixed liquid usually changes into a slurry.

The metal element A is at least one element selected from the group consisting of Nb, Ta, W, Ti, Zr, Re, Fe, Ni, Co, Sn, Tl, Cu, rare earth elements, and alkali metal elements.

Examples of the A-containing compound which is used in the invention include oxides, nitrates, carboxylates, oxonates, and oxalates. The insoluble A-containing compound may be dispersed in and mixed with water. In this case, by jointly using oxalic acid, etc., the compound can be dissolved in water.

An addition amount of the A-containing compound is an amount such that when Mo is defined as 1, the metal element A is from 0.001 to 3.0 in terms of an atomic ratio of the metal in the resulting metal oxide catalyst. In the subject catalyst, in the case where when Mo is defined as 1, the proportion of the metal element A is less than 0.001, deterioration of the resulting catalyst is liable to occur. On the other hand, in the case where it exceeds 3.0, the activity of the resulting catalyst becomes low, and the conversion of propane becomes worse.

In the step (4), by adding ammonia water and nitric acid or ammonium nitrate in a mixed liquid as obtained by mixing the A-containing compound with the reaction liquid as obtained in the step (3), the performance of the resulting metal oxide catalyst is further enhanced. With respect to preferred amounts of ammonia water and nitric acid or ammonium nitrate to be used, the amount of ammonia water is an amount containing 0.4 or more of ammonia in terms of a molar ratio to the metal A, and the amount of nitric acid or ammonium nitrate is an amount containing 2.0 or more of a nitric acid ion in terms of a molar ratio to the metal A, respectively.

Step (5)

In the step (5), the mixed liquid in the state of slurry as obtained in the foregoing step (4) is evaporated to dryness, and the resulting dried material is dried and then calcined.

As a method for removing water from the foregoing mixed liquid, there are enumerated a variety of conventionally known methods such as evaporation to dryness and spray drying. In the case of evaporation to dryness, though the water may be evaporated merely by heating the mixed liquid, by blowing an inert gas such as nitrogen and air during the evaporation to dryness, it is possible to efficiently achieve evaporation to dryness. A temperature of the evaporation to dryness is preferably from 50 to 130° C.

Next, the dried material as obtained by the foregoing operation is calcined. It is preferable that the calcination is carried out on two stages. First of all, the calcination is carried out at a temperature of from 250 to 380° C., and preferably from 280 to 330° C. for from 2 to 20 hours, and preferably from 3 to 10 hours in the presence of oxygen. Thereafter, the resulting material is further calcined in an inert gas wherein no oxygen is present at a temperature of from 500 to 660° C., and preferably from 570 to 620° C. for from 0.5 to 6 hours, and preferably from 1 to 3 hours. In this way, it is possible to produce the metal oxide catalyst according to the invention.

Incidentally, the determination of the contents of metal elements in the metal oxide catalyst as obtained by the foregoing calcining can be carried out by fluorescent X-ray analysis.

Though the metal oxide catalyst as obtained by the foregoing method can be used as it is, it is preferable that the metal oxide catalyst is ground in an appropriate particle size to increase a surface area of the catalyst and then provided for use. As a grinding method, known dry-type grinding method and wet-type grinding method can be employed. Specific examples of a grinding device include a mortar and a ball mill. In the case of wet-type grinding, as grinding assistants, water, alcohols, and the like are enumerated. The particle size of the catalyst after grinding is preferably not more than 20 µm, and more preferably not more than 5 µm.

Though the metal oxide catalyst can be used in a non-supported state, it can also be used by supporting it on a known carrier having an appropriate particle size, such as silica, alumina, silica-alumina, and silicon carbide. The supporting amount is not particularly limited but follows a conventional supporting amount.

A process for producing acrylic acid from propane by using the metal oxide catalyst as produced by the foregoing production process will be hereunder described.

By introducing propane and oxygen gas as raw materials of the production of acrylic acid into a reactor having the metal oxide catalyst charged therein, propane is catalytically oxidized by the metal oxide catalyst, thereby generating acrylic acid.

The reaction temperature is preferably from 300 to 600° C., and more preferably from 350 to 500° C. Propane and oxygen gas can be separately introduced into the reactor, the both of which are then mixed within the reactor; and the both can be mixed in advance and then introduced into the reactor.

Examples of the oxygen gas include pure oxygen gas and air, or a diluted gas thereof with nitrogen, steam or a carbon dioxide gas.

In the case where propane and air are used as raw materials, the proportion of air to propane is preferably not more than 30 times, and more preferably from 0.2 to 20 times in terms of a volume ratio.

The space velocity (hereinafter referred to as "SV") of the whole of the raw material gases is suitably adjusted from 1,000 to 8,000 hr$^{-1}$. When the space velocity is less than 1,000 hr$^{-1}$, a yield of acrylic acid per unit mass of the catalyst becomes low, while when it exceeds 8,000 hr$^{-1}$, the conversion is lowered.

Though the unreacted raw material propane present in a reaction gas to be discharged from an outlet of the reactor or propylene as an intermediate can be used as a fuel as it is, the unreacted raw material propane or propylene as an intermediate which has been separated from other components in the reaction gas can be returned into the reactor and reused.

The metal oxide catalyst as produced by the invention can also be applied to ammoxidation of propane synthesizing acrylonitrile in a high yield. The ammoxidation condition substantially follows the foregoing vapor phase catalytic oxidation condition of propane.

The invention will be more specifically described below with reference to the Examples and Comparative Examples. Incidentally, in the following respective Examples (exclusive of Example 4) and Comparative Examples, the respective raw materials were blended such that a molar ratio of the respective metals constituting the resulting metal oxide catalysts became the following value. A molar ratio of the respective metals in a metal oxide catalyst as obtained in Example 4 is described later.

Mo/V/Te/Nb=1.0/0.25/0.13/0.12

The metal oxide catalyst as obtained in each of the Examples was once tablet-molded, and the molded particle was pulverized into a size of from 16 to 30 mesh and provided for use.

1.1 mL (about 1.0 g) of the catalyst as produced in each of the Examples was charged in a quartz-made reaction tube having an inner diameter of 10 mm. The reaction tube was heated at 400° C., and a mixed gas containing 6.4% by volume of propane, 9.6% by volume of oxygen, 36.1% by volume of nitrogen and 47.7% by volume of steam was fed into the reaction tube at a space velocity of 3,924 hr$^{-1}$, thereby producing acrylic acid.

On the basis of results obtained by composition analysis of the respective components as formed in the reaction product, a conversion of propane and a selectivity of acrylic acid (all of which are on a molar basis) were calculated according to the following expressions. The results except those of Example 4 are shown in Table 1. In Table 1, AA stands for acrylic acid; and P stands for propane.

Conversion of propane (%)=100×[(Fed propane)−(Unreacted propane)]/(Fed propane)

Selectivity of acrylic acid (%)=100×(Formed acrylic acid)/[(Fed propane)−(Unreacted propane)]

Yield of acrylic acid (%)=(Conversion of propane)×(Selectivity of acrylic acid)/100

EXAMPLE 1

In a 500-mL glass-made flask, 3.64 g of tellurium dioxide and 60 mL of distilled water were charged, to which was then added 2.8 g of hydrazine monohydrate (80% by mass as hydrazine) at 80° C. while stirring at a rate of 300 rpm, followed by keeping under this condition for 12 hours. With a lapse of time, the initially white powder was ultimately changed to a black suspension via a gray color, thereby obtaining its dispersion.

The resulting dispersion was filtered by filter paper to obtain a black solid and a transparent and colorless filtrate. The solid on the filter paper was washed with 200 mL of distilled water. After washing, the solid remaining on the filter paper was collected in a sample bottle while diluting with distilled water to obtain 80 mL of an aqueous dispersion (containing 0.28 mole as metallic tellurium).

This aqueous dispersion was divided into two equal parts while stirring. The half was dried at 50° C. for 2 hours and then used as a sample for X-ray diffraction analysis and electron microscopic observation.

As a result of the X-ray diffraction analysis, the resulting black powder exhibited diffraction lines at angles of 22.98, 27.52, 38.24, 40.42, 43.32, 45.88 and 49.62° in terms of 2θ, and the phase of tellurium dioxide was not detected. Thus, the black powder is assigned to a crystal line of pure metallic tellurium.

As shown in FIG. 1, the particle shape of the black powder was of an acicular crystal having a size of 0.1 μm in diameter and several μm in length, and a scattering of the size of the respective crystals was small.

Separately, in a 500-mL glass-made flask, 2.56 g of ammonium metavanadate, 15.45 g of ammonium molybdate, and 50 mL of distilled water were charged and dissolved while stirring at a temperature of the boiling point of water. The foregoing half of the metallic tellurium-containing aqueous dispersion was added to the resulting solution, and the mixture was heat treated for one hour. Thereafter, the flask having the resulting reaction liquid charged therein was cooled to 30° C. by ice water.

Separately, 4.41 g of oxalic acid and 1.74 g of niobic acid were dissolved in 70 mL of distilled water to prepare an aqueous solution of the ambient temperature. This aqueous solution was added to the foregoing reaction liquid. The resulting mixed liquid was vigorously stirred for 10 minutes, with which was then mixed 2.5 g of ammonium nitrate. Thereafter, the mixture was concentrated by heating and further evaporated to dryness at 120° C.

The resulting dried material was calcined in air at 300° C. for 5 hours. Thereafter, calcination was carried out in a nitrogen gas atmosphere at 600° C. for 2 hours to obtain a metal oxide catalyst. As described previously, the resulting catalyst was processed into a size of from 16 to 30 mesh and then used for production reaction of acrylic acid.

EXAMPLE 2

In a ceramics-made pot for grinding having a volume of 500 mL, 3.64 g of tellurium dioxide, 2.8 g of hydrazine monohydrate (80% by mass as hydrazine), and 2.6 g of distilled water were charged and mixed. Next, 25 zirconia balls having a size of 10 mm (density: 6.0 g/cm$^3$) and 5 balls of the same material quality having a size of 20 mm were then charged in the pot. The foregoing pot was placed on two rotary rolls and subjected to grinding treatment by rotating at a rotational speed of 170 rpm for 12 hours.

The resulting black slurry was filtered by filter paper to obtain a solid and a transparent and colorless filtrate. The solid on the filter paper was washed with 200 mL of distilled water. Thereafter, the solid was dispersed in distilled water to obtain 80 mL of an aqueous dispersion (containing 0.28 mole as metallic tellurium). This aqueous dispersion was divided into two equal parts while stirring.

Figure 2:
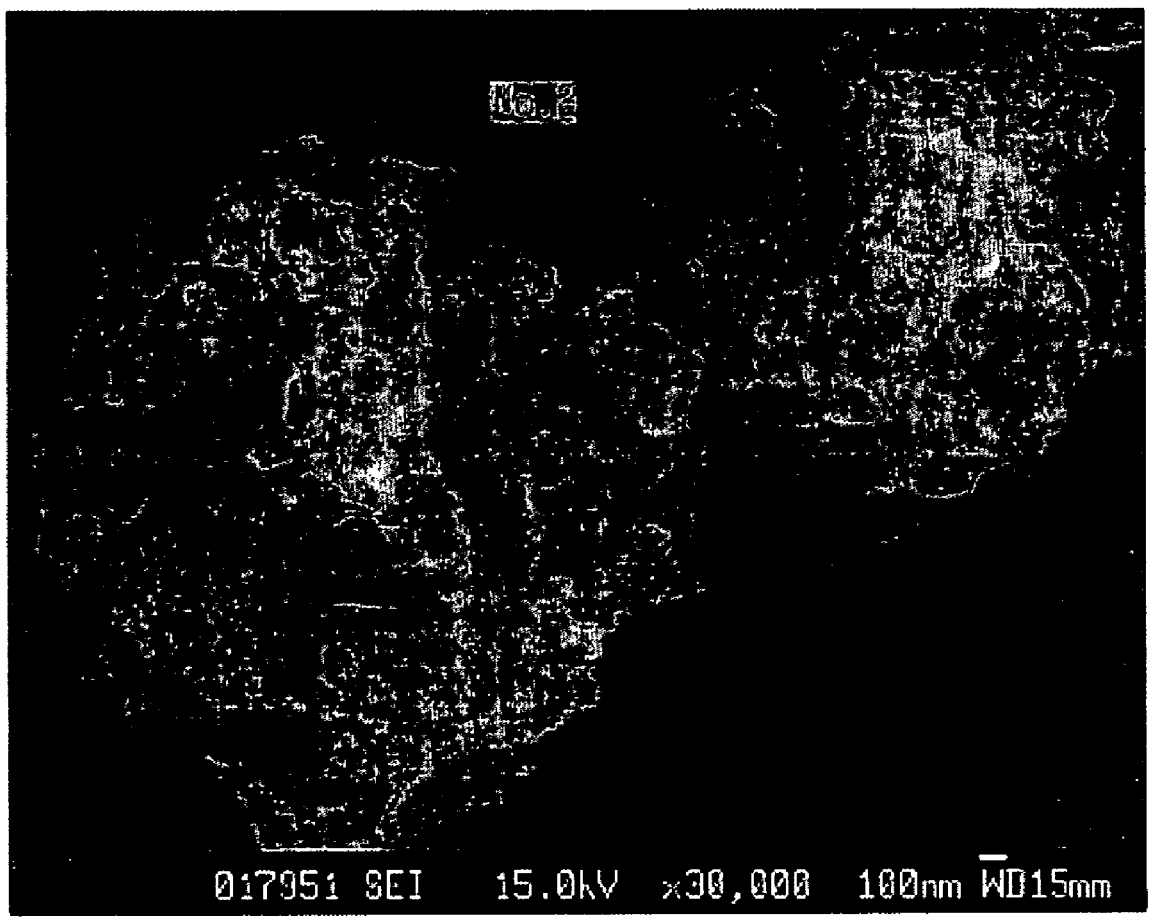
FIG. 2 shows an SEM (scanning electron microscope) image of metallic tellurium particles as obtained in Example 2.

The half was dried at 50° C. for 2 hours, the resulting black powder was provided for measurements of X-ray diffraction analysis and electron microscopic observation. The results of the X-ray diffraction analysis were the same as in Example 1, and it was noted that the resulting black powder is a crystal of pure metallic tellurium. As shown in FIG. 2, the particle shape of the black powder was of an agglomerate having a size of several μm and composed of a primary particle having a size of about 0.1 μm.

A catalyst was prepared by the same operation as in Example 1 by using the foregoing half of the metallic tellurium-containing aqueous dispersion. Acrylic acid was produced under the same condition as in Example 1 by using the resulting catalyst.

EXAMPLE 3

In a 500-mL glass-made flask, 5.24 g of telluric acid and 60 mL of distilled water were charged and dissolved with stirring at room temperature. 2.8 g of hydrazine monohydrate (80% by mass as hydrazine) was added to this solution. A colorless and transparent solution was changed to black slurry at the same time of adding the reductant.

Figure 3:
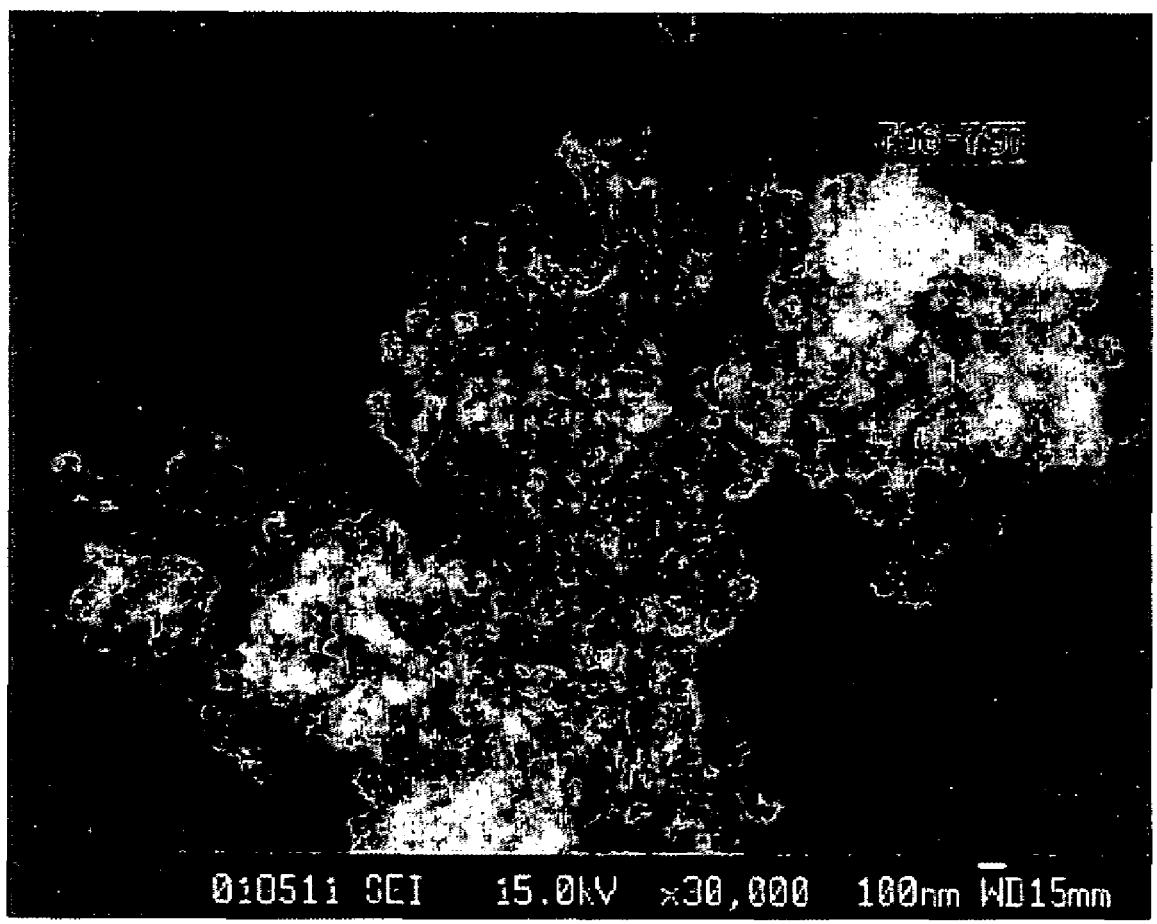
FIG. 3 shows an SEM (scanning electron microscope) image of metallic tellurium particles as obtained in Example 3.

The resulting black slurry was filtered by filter paper. Thereafter, the same operation as in Example 1 was followed to obtain an agglomerate of a fine particle having a particle size of about 0.05 μm as shown in FIG. 3. A catalyst was produced by calcining the agglomerate under the same condition as in Example 1. Acrylic acid was produced under the same condition as in Example 1 by using the resulting catalyst.

EXAMPLE 4

In a 500-mL glass-made flask, 3.64 g of tellurium dioxide and 60 mL of distilled water were charged, to which was then added 2.8 g of hydrazine monohydrate (80% by mass as hydrazine) at 80° C. while stirring at a rate of 300 rpm, followed by keeping under this condition for 12 hours. With a lapse of time, the initially white powder was ultimately changed to a dispersion of black suspension via a gray color. Thereafter, the same operation as in Example 1 was followed to obtain an aqueous dispersion of metallic tellurium.

Separately, in a 500-mL glass-made flask, 2.66 g of ammonium metavanadate, 3.0 g of ammonium molybdate, and 50 mL of distilled water were charged and dissolved while stirring at a temperature of the boiling point of water. The foregoing half of the metallic tellurium dispersion was added to the resulting solution, and the mixture was heat treated for one hour. Thereafter, 12.45 g of ammonium molybdate was dissolved in the foregoing reaction liquid, to which was further added dropwise 1.4 g of 30% ammonia water, and after elapsing for several minutes while stirring, the reaction liquid reached 60° C. 5.89 g of oxalic acid and 2.32 g of niobic acid were dissolved in 160 mL of distilled water to prepare an aqueous solution of the ambient temperature. This aqueous solution was added to the foregoing reaction liquid. After vigorously stirring the resulting mixed liquid for 10 minutes, 3.5 g of ammonium nitrate was mixed with this mixed liquid. Thereafter, the mixture was concentrated by heating and further evaporated to dryness at 120° C. by using a dryer.

The resulting dried material was calcined in air at 320° C. for 1.5 hour. Thereafter, calcination was carried out under a condition at 590° C. for 1.5 hour to obtain a metal oxide catalyst. A molar ratio of the respective metals in the resulting metal oxide catalyst is as follows.

Mo/V/Te/Nb=1.0/0.26/0.13/0.16

The foregoing metal oxide was used as a catalyst in the production of acrylic acid in the same manner as in Example 1. As a result, the conversion of propane was 62.7%, the selectivity of acrylic acid was 81.8%, and the yield of acrylic acid was 51.3%.

COMPARATIVE EXAMPLE 1

In a 500-mL glass-made flask, 2.56 g of ammonium metavanadate, 15.45 g of ammonium molybdate, and 50 mL of distilled water were charged and dissolved while stirring at a temperature of the boiling point of water. 1.45 g of a powder of commercially available metallic tellurium (mean particle size: 150 μm) was added to the resulting solution, and the mixture was heated for one hour.

In steps after heating, operations exactly the same as in Example 1 were followed to produce a catalyst. Acrylic acid was produced in the same manner as in Example 1 by using this catalyst.

COMPARATIVE EXAMPLE 2

A catalyst was produced in the same operations as in Comparative Example 1, except that in Comparative Example 1, after adding the powder of metallic tellurium to the foregoing solution, the mixture was heated for 5 hours. Acrylic acid was produced under the same condition as in Example 1 by using this catalyst.

COMPARATIVE EXAMPLE 3

In a 500-mL glass-made flask, 2.56 g of ammonium metavanadate, 15.45 g of ammonium molybdate, 2.62 g of telluric acid, and 90 mL of distilled water were charged and dissolved while stirring at a temperature of the boiling point of water. The flask having the resulting reaction liquid charged therein was cooled to 30° C. by ice water.

Separately, 4.41 g of oxalic acid and 1.74 g of niobic acid were dissolved in 70 mL of distilled water to prepare an aqueous solution of the ambient temperature. This aqueous solution was added to the foregoing liquid which had been cooled to 30° C. The resulting mixed liquid was vigorously stirred for 10 minutes, with which was then mixed 2.5 g of ammonium nitrate. Thereafter, the mixture was concentrated by heating and further evaporated to dryness at 120° C.

The resulting dried material was calcined in air at 300° C. for 5 hours. Thereafter, calcination was carried out in a nitrogen gas atmosphere at 600° C. for 2 hours to obtain a metal oxide catalyst. Results obtained by using this for production reaction of acrylic acid are shown in Table 1.

COMPARATIVE EXAMPLE 4

In a 500-mL glass-made flask, 2.56 g of ammonium metavanadate, 15.45 g of ammonium molybdate, 1.82 g of tellurium dioxide, and 90 mL of distilled water were charged and stirred at a temperature of the boiling point of water for one hour. The flask having the resulting slurry charged therein was cooled to 30° C. by ice water.

Separately, 4.41 g of oxalic acid and 1.74 g of niobic acid were dissolved in 70 mL of distilled water to prepare an aqueous solution of the ambient temperature. This aqueous solution was added to the foregoing liquid which had been cooled to 30° C. The resulting mixed liquid was vigorously stirred for 10 minutes, with which was then mixed 2.5 g of ammonium nitrate. Thereafter, the mixture was concentrated by heating and further evaporated to dryness at 120° C.

The resulting dried material was calcined in air at 300° C. for 5 hours. Thereafter, calcination was carried out in a nitrogen gas atmosphere at 600° C. for 2 hours to obtain a metal oxide catalyst. Results obtained by using this for production reaction of acrylic acid are shown in Table 1.

TABLE 1

|  | Conversion of P (%) | Selectivity of AA (%) | Yield of AA (%) |
|---|---|---|---|
| Example 1 | 60.3 | 78.5 | 47.3 |
| Example 2 | 58.6 | 80.9 | 47.4 |
| Example 3 | 56.0 | 80.8 | 45.2 |
| Comparative Example 1 | 15.5 | 59.8 | 9.3 |
| Comparative Example 2 | 9.6 | 57.5 | 5.5 |
| Comparative Example 3 | 25.6 | 60.5 | 15.5 |
| Comparative Example 4 | 3.6 | 57.9 | 2.1 |

INDUSTRIAL APPLICABILITY

According to the production process of the invention, a fine particle of metallic tellurium having high reactivity can be allowed to react with other metal in an aqueous medium, whereby a metal oxide catalyst with high performance can be obtained. When this catalyst is used for production reaction of acrylic acid by vapor phase catalytic oxidation reaction of propane, acrylic acid can be produced in a high yield. Furthermore, the present catalyst can be used for ammoxidation of propane, whereby acrylonitrile can be obtained in a high yield.

The invention claimed is:

1. A process for producing a metal oxide catalyst represented by the following composition formula, which is characterized by allowing a fine particle of metallic tellurium as obtained by reducing a $Te^{4+}$ compound or a $Te^{6+}$ compound in the presence of a reductant and water or an organic solvent to react in the presence of an Mo compound, a V compound, a compound containing an A element and water and then drying and calcining $MoV_iTe_jA_kO_y$    Composition formula (wherein A is at least one element selected from Nb, Ta, W, Ti, Zr, Re, Fe, Ni, Co, Sn, Tl, Cu, rare earth elements, and alkali metal elements, i and j are each from 0.01 to 1.5, and j/i is from 0.3 to 1.0; k is from 0.001 to 3.0; and y is the number to be determined by the oxidized state of other elements).

2. A process for producing a metal oxide catalyst represented by the following composition formula, which is characterized by employing a process comprising the following step (1), step (2), step (3), step (4) and step (5):

Step (1): a step for reducing a $Te^{4+}$ compound or a $Te^{6+}$ compound in the presence of a reductant and water or an organic solvent to obtain a dispersion containing a fine particle of metallic tellurium;

Step (2): a step for removing the unreacted reductant and organic solvent contained in said dispersion as obtained in said step (1) to obtain an aqueous dispersion containing a fine particle of metallic tellurium;

Step (3): a step for mixing the aqueous dispersion containing a fine particle of metallic tellurium as obtained in said step (2) with an $Mo^{6+}$ compound and a $V^{5+}$ compound and allowing the mixture to react at a temperature of 40° C. or higher for one hour or more to obtain a reaction liquid;

Step (4): a step for mixing the reaction liquid as obtained in said step (3) with a compound containing the following A element to obtain a mixed liquid; and Step (5): a step for evaporating to dryness the mixed liquid as obtained in said step (4), drying the resulting dried material and further calcining it $$MoV_iTe_jA_kO_y \qquad \text{Composition formula}$$

(wherein A is at least one element selected from Nb, Ta, W, Ti, Zr, Re, Fe, Ni, Co, Sn, Tl, Cu, rare earth elements, and alkali metal elements. i and j are each from 0.01 to 1.5, and j/i is from 0.3 to 1.0; k is from 0.001 to 3.0; and y is the number to be determined by the oxidized state of other elements).

3. The process for producing a metal oxide catalyst according to claims 1, wherein a primary particle of the metallic tellurium has a size of not more than 4.0 μm.

4. The process for producing a metal oxide catalyst according to claim 2, wherein a primary particle of the metallic tellurium has a size of not more than 4.0 μm.

5. A process for producing acrylic acid, which is characterized by subjecting propane to oxidation by vapor phase catalytic reaction in the presence of the metal oxide as produced by the process according to any one of claims 1 to 4.

6. A process for producing acrylonitrile, which is characterized by subjecting propane to ammoxidation in the presence of the metal oxide as produced by the process according to any one of claims 1 to 4.

* * * * *